United States Patent [19]
Malloy et al.

[11] 4,323,714
[45] Apr. 6, 1982

[54] ALKYLATION OF HYDROXY-SUBSTITUTED AROMATIC COMPOUNDS

[75] Inventors: Thomas P. Malloy, Lake Zurich; Dusan J. Engel, Des Plaines, both of Ill.

[73] Assignee: UOP Inc., Des Plaines, Ill.

[21] Appl. No.: 208,953

[22] Filed: Nov. 20, 1980

[51] Int. Cl.$^3$ .................. C07C 37/11; C07C 39/08
[52] U.S. Cl. .................................. 568/766; 568/788; 568/793; 568/736; 568/804; 568/720
[58] Field of Search ............... 568/804, 766, 790, 793, 568/736, 780, 784, 785, 788, 720, 719

[56] References Cited

U.S. PATENT DOCUMENTS 3,422,157  1/1969  Kaufman et al. ............... 568/790
3,932,537  1/1976  Wetzel et al. .................. 568/793

*Primary Examiner*—Werren B. Lone
*Attorney, Agent, or Firm*—James R. Hoatson, Jr.; Raymond H. Nelson; William H. Page II

[57] ABSTRACT

Hydroxy-substituted aromatic compounds may be alkylated by treatment with an alkylating agent such as an olefin or an alcohol at a temperature in the range of from about 50° to about 200° C. and a pressure in the range of from about atmospheric to about 100 atmospheres in the presence of a fluoro-substituted resin. The resulting product will comprise both mono- and di-alkylated hydroxy-substituted aromatic compounds.

8 Claims, No Drawings

4,323,714

ALKYLATION OF HYDROXY-SUBSTITUTED AROMATIC COMPOUNDS

BACKGROUND OF THE INVENTION

Alkylated hydroxy-substituted aromatic compounds are useful in the chemical industry for a variety of purposes. For example, t-butylhydroquinone has been shown to possess excellent anti-oxidant properties with a concomitant low toxicity. Therefore, it is possible to utilize this compound as an anti-oxidant in the food industry being especially useful as an anti-oxidant for fats, lards, oils and fat-containing foods, either by incorporation into the food stuff itself or by being incorporated in the material which is used to encase or wrap the particular food stuff. Likewise, t-butylphenol will find a use as a plasticizer, as an intermediate for anti-oxidants, as a pore-point depressor, an emulsion breaker for petroleum oils and some plastics, as an intermediate for synthetic resins, surface active agents, perfumes, etc.

Di-t-butylphenol and di-t-butylhydroquinone have also found many uses as anti-oxidants. 2,6-di-t-butylphenol is an anti-oxidant for gasoline and 4-methyl-2,6-di-t-butylphenol is an anti-oxidant in the food industry and in rubbers, paints and plastics. 2,5-di-t-butylhydroquinone is a polymer inhibitor and an anti-oxidant in vegetable fats and oils as well as a stabilizer against the ultraviolet deterioration of rubber.

One method for effecting the alkylation of these compounds is to alkylate a hydroxy-substituted aromatic compound like hydroquinone with an alkylating agent in the presence of an acidic catalyst and in a reaction medium comprising a hydrocarbon solvent. However, the amount of the di-alkylated product is usually low.

As will hereinafter be shown in greater detail, it has now been discovered that by effecting the alkylation reaction in the presence of a certain catalytic composition of matter, it is possible to obtain a higher degree or greater yield of di-alkylated product. In addition, it is also possible by utilizing this catalyst to effect the reaction at a relatively low temperature, thereby decreasing the amount of energy required with a greater savings of cost.

DETAILED DESCRIPTION OF THE INVENTION

This invention relates to a process for the alkylation of hydroxy-substituted aromatic compounds. More specifically, the invention is concerned with a process for the alkylation of hydroxy-substituted aromatic compounds to obtain a greater yield of di-alkylated product.

As will hereinafter be shown in greater detail, it has now been discovered that the alkylation of hydroxy-substituted aromatic compounds may be effected in an organic reaction medium utilizing, as a catalyst for the reaction, a resinous compound. By utilizing this type of catalyst, the reaction may be effected under relatively mild operating conditions of temperature and pressure to obtain a di-alkylated product.

It is therefore an object of this invention to provide a process for the preparation of alkylated hydroxy-substituted aromatic compounds.

A further object of this invention is to provide a process for effectively alkylating hydroxy-substituted aromatic compounds under relatively mild operating conditions in the presence of certain catalytic compounds of matter.

In one aspect an embodiment of this invention is found in a process for the alkylation of a hydroxy-substituted aromatic compound which comprises treating said hydroxy-substituted aromatic compound with an alkylating agent at alkylation conditions in the presence of a fluoro-substituted resin, and recovering the resultant alkylated hydroxy-substituted aromatic compound.

A specific embodiment of this invention is found in the process for the alkylation of a hydroxy-substituted aromatic compound which comprises treating hydroquinone with isobutylene at a temperature in the range of from about 50° to about 200° C. and a pressure in the range of from about atmospheric to about 100 atmospheres in the presence of a perfluorosulfonic acid resin and recovering the resultant di-t-butylhydroquinone.

Other objects and embodiments will be found in the following further detailed description of the invention.

As hereinbefore set forth, the present invention is concerned with a process for the alkylation of hydroxy-substituted aromatic compounds. The process is effected by treating a hydroxy-substituted aromatic compound with an alkylating agent at alkylation conditions which include temperatures in the range of from about 50° to about 200° C. and a pressure in the range of from about atmospheric to about 100 atmospheres. Examples of hydroxy-substituted aromatic compounds which may be subjected to alkylation will include mono-substituted aromatic compounds such as phenol, 1-hydroxynaphthalene, 2-hydroxynaphthalene, anthracene, 2-hydroxyanthracene, 1-hydroxyphenanthrene, 2-hydroxyphenanthrene, 3-hydroxyphenanthrene, etc; dihydroxy-substituted aromatic compounds such as 1,2-dihydroxybenzene (catechol), 1,4-dihydroxybenzene (hydroquinone), 1,2-dihydroxynaphthalene, 1,4-dihydroxynaphthalene, 1,5-dihydroxynaphthalene, 1,2-dihydroxyanthracene, 1,4-dihydroxyanthracene, etc.

The alkylating agents which are employed as starting materials in the process of this invention will include olefins containing from 2 to about 10 carbon atoms in length and alcohols containing from 1 to about 10 carbon atoms in length. Some specific examples of these alkylating agents will include olefins such as ethylene, propylene, 1-butylene, 2-butylene, isobutylene, 1-pentene, 2-pentene, 2-methylpentene-2, 3-methylpentene-2, 1-hexene, 2-hexene, 3-hexene, 1-heptene, 2-heptene, 3-heptene, the isomeric octenes, nonenes, decenes, etc; alcohols such as methyl alcohol, ethyl alcohol, n-propyl alcohol, isopropyl alcohol, n-butyl alcohol, t-butyl alcohol, n-pentyl alcohol, sec-pentyl alcohol as well as the isomeric hexyl, heptyl, octyl, nonyl, and decyl alcohols etc. It is to be understood that the aforementioned hydroxy-substituted aromatic compounds and alkylating agents comprising olefins and alcohols are only representative of the class of compounds which may be employed, and that the present invention is not necessarily limited thereto.

The alkylation process of the present invention is effected in an organic solvent which is utilized as the reaction medium and also in the presence of a catalyst comprising a fluoro-substituted resin. In the preferred embodiment of the invention, the fluoro-substituted resin comprises a fluoro-substituted sulfonic resin and particularly a perfluorosulfonic acid resin. Examples of organic compounds which may be employed as the reaction medium will include non-polar solvents such as xylene, toluene, benzene, etc. or aliphatic ketones which may contain from about 3 to about 8 carbon atoms such as acetone, 2-butanone, 2-pentanone, 2-hexanone, 2-heptanone, 2-octanone, 3-pentanone, 3-hexanone, 3-heptanone, 3-octanone, etc.

The process of this invention may be effected in any suitable manner and may comprise either a batch or continuous-type operation. For example, when a batch-type operation is to be performed, a quantity of the catalyst comprising a fluoro-substituted resin which may be in granular form is placed in the desired reaction apparatus. Thereafter, the apparatus is purged of air by charging nitrogen through the apparatus and, following the removal of the air, the liquid feed is then pumped into the reactor. The liquid feed will comprise the hydroxy-substituted aromatic compound admixed with the orgainic solvent of the type hereinbefore set forth. In addition, the alkylating agent is also charged to the reaction apparatus until the desired amount has been admixed thereto. Alternatively, the alkylating agent may be added at the reaction temperature. In the event that the alkylating agent is in gaseous form, the preferred reaction apparatus will comprise an autoclave of the stirring, mixing, or rotating type, while if the alkylating agent is in liquid form, the reaction vessel may comprise an alkylation flask or tube. The apparatus is heated to the desired operating temperature and maintained thereat for a predetermined period of time which may range from about 0.2 up to about 10 hours or more in duration. As hereinbefore set forth, the alkylation reaction may be effected over a relatively wide range of temperatures and pressures, the particular operating conditions being selected with respect to the starting materials comprising the hydroxy-substituted aromatic compound and the alkylating agent. In the event that superatmospheric pressures are employed to effect the alkylation reaction, said pressures may be afforded by the autogenous pressure of the alkylating agent, if in gaseous form, or they may be afforded by the introduction of a substantially inert gas such as nitrogen, argon, helium, etc. into the reaction vessel.

Upon completion of the desired residence time, the reaction apparatus is allowed to return to room temperature and any excess pressure, if present, is discharged. The reactor is opened and the reaction mixture is recovered therefrom. Thereafter, the reaction mixture is separated from the catalyst by conventional means such as filtration, or decantation, and the former is then further subjected to conventional means of separation such as fractional distillation, crystallization, etc. whereby the alkylated hydroxy-substituted aromatic compound is separated from unreacted starting materials.

It is also contemplated within the scope of this invention that the alkylation process may be effected in a continuous-type of operation. When this type of operation is employed, the starting materials comprising the hydroxy-substituted aromatic compound and the alkylating agent are continuously charged to a reaction zone which is maintained to the proper operating conditions of temperature and pressure and which contains the fluoro-substituted sulfonic acid resin catalyst. The starting materials may be charged to the reaction zone through separate lines or, if so desired, they may be admixed with the solvent, and the resulting mixture charged thereto in a single stream. After a predetermined period of residence time in the reactor, the effluent is continuously discharged and again subjected to separation means whereby the alkylated product is separated from unreacted starting materials and recovered, the latter being recycled to the reaction zone to form a portion of the feed stock.

Inasmuch as the fluoro-substituted sulfonic acid resin is in solid form, the continuous method of operation may be effected in various ways. For example, the catalyst may be positioned in the reactor zone as a fixed bed and the reactants passed through said bed in either an upward or downward flow. Another form of operation comprises the moving bed type in which the catalyst is moved through the reaction zone while the starting materials are contacted by the catalyst bed either in a concurrent or countercurrent flow. A third method of effecting a continuous type of operation comprises the slurry type in which the catalyst is introduced into the reaction zone as a slurry in one or both of the starting materials.

Examples of alkylated hydroxy-substituted aromatic compounds which may be obtained by the process of the present invention will include methylphenol (cresol), dimethylphenol (xylenol), ethylphenol, diethylphenol, propylphenol, dipropylphenol, isopropylphenol, diisopropylphenol, n-butylphenol, n-dibutylphenol, t-butylphenol, pentylphenol, dipentylphenol; methylcatechol, dimethylcatechol, ethylcatechol, diethylcatechol, propylcatechol, dipropylcatechol, isopropylcatechol, diisopropylcatechol, n-butylcatechol, n-dibutylcatechol, t-butylcatechol, pentylcatechol, dipentylcatechol; methylhydroquinone, dimethylhydroquinone, ethylhydroquinone, diethylhydroquinone, propylhydroquinone, dipropylhydroquinone, isopropylhydroquinone, diisopropylhydroquinone, n-butylhydroquinone, n-dibutylhydroquinone, t-butylhydroquinone, pentylhydroquinone, dipentylhydroquinone; methylhydroxynaphthalene, dimethylhydroxynaphthalene, ethylhydroxynaphthalene, diethylhydroxynaphthalene, propylhydroxynaphthalene, dipropylhydroxynaphthalene, isopropylhydroxynaphthalene, diisopropylhydroxynaphthalene, n-butylhydroxynaphthalene, di-n-butylhydroxynaphthalene, t-butylhydroxynaphthalene, di-t-butylhydroxynaphthalene, pentylhydroxynaphthalene, dipentylhydroxynaphthalene, etc. It is to be understood that the aforementioned alkylated hydroxy-substituted aromatic compounds are only representative of the class of compounds which may be prepared and that the present invention is not necessarily limited thereto.

The following examples are given to illustrate the process of this invention. However, it is to be understood that said examples are merely for purposes of illustration, and that the present process is not necessarily limited thereto.

EXAMPLE I

In this example, a flask was loaded with 4.0 grams of a perfluorosulfonic resin sold under the registered trademark Nafion by the DuPont Company. The catalyst was prepared by placing the resin pellets, which were in the potassium form, in hydrochloric acid and stirring the mixture. After a sufficient length of time, the resin was filtered and superficially washed. The treatment with hydrochloric acid was repeated an additional four times in order to insure a greater than 95% conversion of the potassium form to the acidic form. Upon completion of the final exchange, the resin was thoroughly washed with water and dried in a vacuum oven at a temperature ranging from about 60° to about 90° C. After placing the catalyst in the flask, it was sealed and purged by treatment with nitrogen to remove the air. Following this, 200 grams of a 17.5% solution of hydroquinone in 2-heptanone (0.32 mole hydroquinone) was charged into the flask followed by introduction of 11.8 grams (0.21 mole) of isobutylene, which was absorbed completely. The contents were stirred and heated to a temperature of 75° C. during a period of 2 hours. The product at the end of this period was subjected to chromatographic analysis which determined that there had been a 27% conversion of hydroquinone and a 66% conversion of isobutylene. The selectivities of the product comprised 33% mono-t-butylhydroquinone and 41% di-t-butylhydroquinone which approximated a weight ratio of 0.6:1 mono-t-butylhydroquinone to di-t-butylhydroquinone.

EXAMPLE II

A reaction flask was loaded with 8.2 grams of Nafion resin in its acidic form, said resin having been prepared in a manner to that set forth in Example I above. Thereafter, 35.0 grams (0.32 mole) of hydroquinone in 200 cc of xylene was added to the flask. The flask was then purged with nitrogen, after which the contents were stirred and brought to a temperature in the range of from about 105° C. to 110° C. Upon reaching this temperature, 11.8 grams (0.21 mole) of isobutylene were introduced into the flask during a period of 0.25 hours. At the end of this period, the reaction mixture was analyzed by means of gas chromatography. It was determined that there had been a 65% conversion of hydroquinone and a 100% conversion of the isobutylene. The analysis also disclosed that the selectivity of the product comprised 39% mono-t-butylhydroquinone and 58% di-t-butylhydroquinone, which approximated a 0.5:1 weight ratio of mono-alkylated product to di-alkylated product.

EXAMPLE III

In this example, a perfluorosulfonic resin catalyst which may be prepared according to the method set forth in Example I above may be placed in a flask which is then purged with nitrogen. Following the purge of the nitrogen, a charge comprising a 20% solution of catechol in a solvent comprising 2-heptanone may be charged to the flask along with t-butyl alcohol. The reaction may be allowed to proceed for a period of four hours while maintaining the reactor at a temperature of about 75° C. At the end of this period, the reaction mixture may be subjected to chromatographic analysis to determine the presence of mono-t-butylcatechol and di-t-butylcatechol.

EXAMPLE IV

In a manner similar to that set forth in Example II, phenol may be subjected to an alkylation procedure utilizing isopropylene as the alkylating agent in the presence of a perfluorosulfonic acid resin catalyst. The reaction may be effected at a temperature of about 100° C. for a period of one hour and thereafter, the reaction mixture may be subjected to chromatographic analysis to determine the presence of isopropylphenol and diisopropylphenol.

EXAMPLE V

In this example, hydroquinone and xylene may be charged to a reactor containing a perfluorosulfonic acid resin catalyst. In addition, the alkylating agent comprising isopropyl alcohol may also be charged to the reactor after which said reactor is heated to an operating temperature of about 75° C. Following a residence time of four hours, the reactor effluent may be withdrawn and subjected to chromatographic analysis to determine the presence of isopropylhydroquinone and diisopropylhydroquinone.

We claim as our invention:

1. A process for the alkylation of a mono- or di-hydroxy-substituted aromatic compound selected from the group consisting of phenol, 1-hydroxynaphthalene, 2-hydroxynaphthalene, anthracene, 2-hydroxyanthracene, 1-hydroxyphenanthrene, 2-hydroxyphenanthrene, 3-hydroxyphenanthrene, 1,2-dihydroxybenzene (catechol), 1,4-dihydroxybenzene (hydroquinone), 1,2-dihydroxynaphthalene, 1,4-dihydroxynaphthalene, 1,5-dihydroxynaphthalene, 1,2-dihydroxyanthracene, and 1,4-dihydroxyanthracene, which comprises treating said mono- or di-hydroxy-substituted aromatic compound with an alkylation agent selected from the group consisting essentially of aliphatic olefins containing from 2 carbon atoms to about 10 carbon atoms in length and alcohols containing from 1 to about 10 carbon atoms in length at a temperature of from about 50° to about 200° C. and a pressure in the range of from about atmospheric pressure to about 100 atmosphere in the presence of a catalyst consisting essentially of a solid perfluorosulfonic acid resin, and recovering the resultant alkylated hydroxy-substituted aromatic compounds.

2. The process as set forth in claim 1 in which said di-hydroxy-substituted aromatic compound is hydroquinone.

3. The process as set forth in claim 1 in which said di-hydroxy-substituted compound is catechol.

4. The process as set forth in claim 1 in which said mono-hydroxy-substituted compound is phenol.

5. The process as set forth in claim 2 in which said alkylating agent is isobutylene and said alkylated hydroxy-substituted aromatic compounds comprise di-t-butylhydroquinone and mono-t-butylhydroquinone.

6. The process as set forth in claim 3 in which said alcohol alkylating agent is t-butyl alcohol and said alkylated hydroxy-substituted aromatic compounds comprise di-t-butylcatechol and mono-t-butylcatechol.

7. The process as set forth in claim 4 in which said olefinic alkylating agent is propylene and said alkylated hydroxy-substituted aromatic compounds are diisopropylphenol and monoisopropylphenol.

8. The process as set forth in claim 2 in which said alcohol alkylating agent is isopropyl alcohol and said alkylated hydroxy-substituted aromatic compounds comprise diisopropylhydroquinone and monoisopropylhydroquinone.

* * * * *